US010254415B2

United States Patent
Matsusaka et al.

(10) Patent No.: US 10,254,415 B2
(45) Date of Patent: Apr. 9, 2019

(54) SCINTILLATOR PANEL FOR X-RAY TALBOT IMAGING APPARATUS, IMAGE DETECTING PANEL FOR X-RAY TALBOT IMAGING APPARATUS, AND X-RAY TALBOT IMAGING APPARATUS

(71) Applicant: Konica Minolta, Inc., Tokyo (JP)

(72) Inventors: Mika Matsusaka, Hino (JP); Kei Isoda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/728,970

(22) Filed: Oct. 10, 2017

(65) Prior Publication Data

US 2018/0106908 A1    Apr. 19, 2018

(30) Foreign Application Priority Data

Oct. 14, 2016 (JP) ................. 2016-202605

(51) Int. Cl.
| | |
|---|---|
| G01T 1/00 | (2006.01) |
| G01T 1/10 | (2006.01) |
| G01N 23/04 | (2018.01) |
| G01N 23/083 | (2018.01) |
| G01T 1/20 | (2006.01) |

(52) U.S. Cl.
CPC ............. *G01T 1/10* (2013.01); *G01N 23/04* (2013.01); *G01N 23/083* (2013.01); *G01T 1/2002* (2013.01); *G01N 2223/505* (2013.01)

(58) Field of Classification Search
None
See application file for complete search history.

(56) References Cited

U.S. PATENT DOCUMENTS

| | | | |
|---|---|---|---|
| 2007/0183580 A1* | 8/2007 | Popescu | A61B 6/00 378/145 |
| 2012/0183124 A1* | 7/2012 | Kaneko | A61B 6/4291 378/62 |
| 2015/0309190 A1* | 10/2015 | Kinoshita | G01T 1/2018 250/486.1 |
| 2017/0052265 A1* | 2/2017 | Fukuda | G01T 1/20 |

OTHER PUBLICATIONS

S. Rutishauser, et al; Structured scintillator for hard x-ray grating interferometry; Applied Physics Letters; vol. 98; 2011; pp. 171107-1 to 171107-3.

* cited by examiner

*Primary Examiner* — Yara B Green
(74) *Attorney, Agent, or Firm* — Lucas & Mercanti, LLP

(57) ABSTRACT

A scintillator panel includes alternately arranged scintillator portions and non-scintillator portions, in which the scintillator portions include a stress-relaxing portion. Preferably, a stress-relaxing portion content in 100% by volume of the scintillator portions is from 2 to 50% by volume.

7 Claims, 5 Drawing Sheets

1···NON-SCINTILLATOR PORTION
2···SCINTILLATOR PORTION

SCINTILLATOR PANEL FOR X-RAY TALBOT IMAGING APPARATUS, IMAGE DETECTING PANEL FOR X-RAY TALBOT IMAGING APPARATUS, AND X-RAY TALBOT IMAGING APPARATUS

Japanese Patent Application No. 2016-202605 filed on Oct. 14, 2016, including description, claims, drawings, and abstract, whose entire disclosure is incorporated herein by reference in its entirety.

TECHNOLOGICAL FIELD

The present invention relates to a scintillator panel for an X-ray Talbot imaging apparatus, an image detecting panel for an X-ray Talbot imaging apparatus, and an X-ray Talbot imaging apparatus.

BACKGROUND

At present, X-ray image diagnosis uses an absorption image obtained by imaging attenuation of X-rays transmitted through an object. On the other hand, since X-rays are a type of electromagnetic waves, recent focus has been on fluctuations of electromagnetic waves, and attempts have been made to image phase shift of X-rays transmitted through an object. While an image obtained by imaging the attenuation of X-rays transmitted through an object is called absorption contrast, an image obtained by imaging the phase shift of X-rays transmitted therethrough is called phase contrast. The imaging technique using phase contrast is higher in sensitivity to light elements as compared to the conventional technique using absorption contrast, and thus is thought to be suitable to capture images of soft tissue of a human body containing many light elements.

However, the phase contrast imaging technique requires use of a synchrotron X-ray source or a microfocus X-ray tube. The use of a synchrotron X-ray source requires a huge facility, and the use of a microfocus X-ray tube cannot secure a sufficient amount of X-rays to image a human body. Accordingly, it has been believed that it is difficult to practically use the technique in ordinary medical facilities.

To solve the above problem, X-ray imaging diagnosis using an X-ray Talbot Lau interferometer (a Talbot system) is expected. The system can acquire a phase contrast image by using an X-ray source conventionally used in medical settings.

As illustrated in FIG. 1, in the X-ray Talbot-Lau interferometer, a grating G0, a grating G1, and a grating G2 are arranged between an X-ray source and an X-ray image detector (Flat Panel Detector: FPD, also referred to as "image detecting panel") to visualize refraction of X-rays caused by an object, as moiré fringes. X-rays emitted from the X-ray source pass through the gratings G0, the object, the gratings G1 and G2 in order, to reach the X-ray image detector.

It has also been considered that an X-ray Talbot imaging apparatus incorporating the Talbot-Lau interferometer employs a scintillator panel in which the scintillator panel forming the X-ray image detector is provided with a grating function, whereby the grating G2 and scintillator portions are integrated.

On the other hand, for example, Non-patent Document 1 discloses a scintillator panel in which a phosphor component (CsI) is filled in grooves formed by etching a silicon wafer.

Usually, from the viewpoint of improvement in luminance, a phosphor component content in scintillator portions is desirably 100% by volume. However, in scintillator panels for an X-ray Talbot imaging apparatus, the thickness of partition walls (also referred to as "non-scintillator portions) between scintillator portions is extremely thin as compared to conventional scintillator panels in which a phosphor is partitioned by partition walls. Due to this, influence of heat generated during operation of the apparatus has led to deformation caused by a thermal expansion difference between the phosphor component and the partition walls, resulting in local cracking and/or phosphor peeling. Thus, it has been difficult to directly use such a conventional scintillator panel for an image detecting panel to apply to an X-ray Talbot imaging apparatus.

DESCRIPTION OF THE RELATED ART

Non-patent document 1: Applied Physics Letter 98, 171107 (2011)

SUMMARY

It is an object of the present invention to provide a scintillator panel for an X-ray Talbot imaging apparatus in which even when heat is generated during operation of the apparatus, local cracking or peeling of a phosphor component due to a thermal expansion difference between the phosphor component and partition walls hardly occurs.

To achieve the abovementioned object, a scintillator panel for an X-ray Talbot imaging apparatus reflecting one aspect of the present invention comprises:

alternately arranged scintillator portions and non-scintillator portions, the scintillator portions including a stress relaxing portion.

BRIEF DESCRIPTION OF THE DRAWINGS

The advantages and features provided by one or more embodiments of the present invention will become more fully understood from the detailed description given hereinbelow and the appended drawings which are given by way of illustration only, and thus are not intended as a definition of the limits of the invention.

FIGS. 2A and 2B are schematic diagrams, each partially depicting a grating G2 and an X-ray image detector in a Talbot-Lau interferometer, in which FIG. 2A depicts an arrangement of a grating G2, a scintillator, and a sensor incorporated in a conventional Talbot-Lau interferometer, and FIG. 2B depicts an arrangement of a scintillator panel according to the present invention in which a grating G2 and scintillator portions are integrated and a sensor;

FIGS. 3A and 3B are schematic diagrams of scintillator panels according to embodiments of the invention, in which FIG. 3A depicts a scintillator panel having a one-dimensional periodic structure, and FIG. 3B depicts a scintillator panel having a two-dimensional periodic structure.

DETAILED DESCRIPTION OF EMBODIMENTS

Hereinafter, one or more embodiments of the present invention will be described with reference to the drawings. However, the scope of the invention is not limited to the disclosed embodiments.

Hereinafter, a description will be given of a scintillator panel for an X-ray Talbot imaging apparatus, an image detecting panel for an X-ray Talbot imaging apparatus, and an X-ray Talbot imaging apparatus according to the present invention will be described. Hereinbelow, the scintillator panel for an X-ray Talbot imaging apparatus according to the invention may also be referred to simply as "scintillator panel".

[Scintillator Panel for X-Ray Talbot Imaging Apparatus]

The scintillator panel according to the present invention has a structure including alternately arranged scintillator portions and non-scintillator portions, in which the scintillator portion includes a stress-relaxing portion. Additionally, the scintillator panel according to the invention preferably includes a support. Here, the non-scintillator portions are also referred to as "partition walls".

Figure 1:
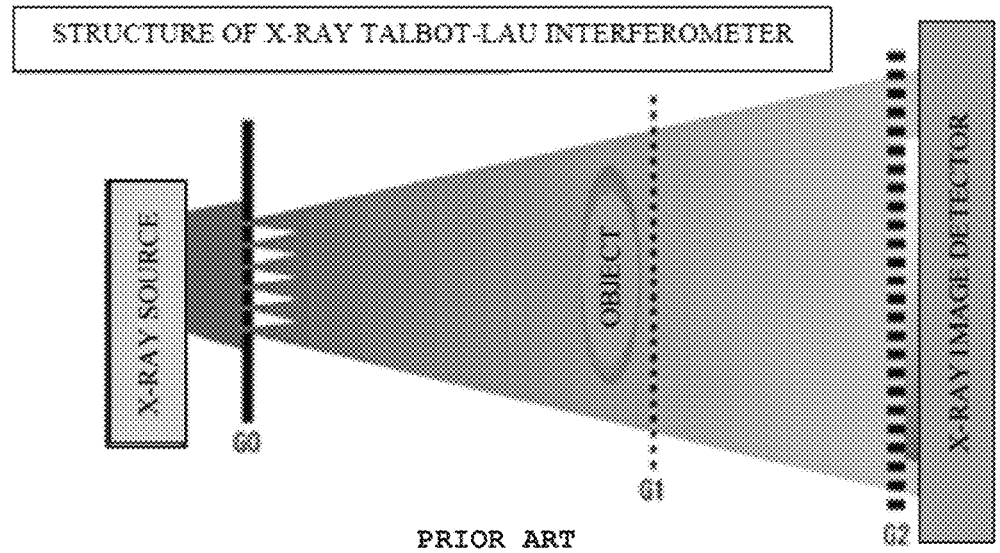
FIG. 1 is a schematic diagram of the structure of a Talbot-Lau interferometer.
Figure 2A:
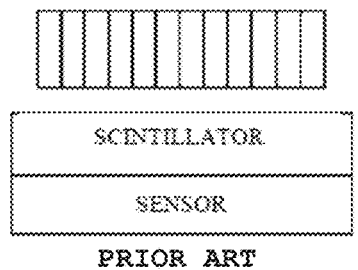
Figure 2B:
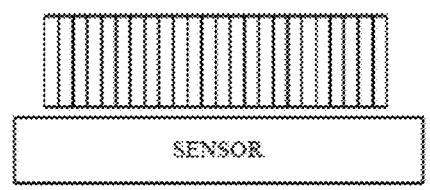

In the Talbot-Lau interferometer, usually, the grating G0, the grating G1, and the grating G2 are arranged between the X-ray source and the X-ray image detector (Flat Panel Detector: FPD), as indicated in FIG. 1. The X-ray image detector includes a scintillator and a sensor (a light-receiving sensor). However, in conventional structures, the grating G2, the scintillator, and the sensor are arranged in order, as indicated in FIG. 2A, which has created a problem in that an X-ray interference pattern obtained by the grating G2 is converted to light by the scintillator and then scattered before reaching the light-receiving sensor, thus failing to obtain a clear image. On the other hand, in the scintillator panel according to the invention, the scintillator portions and the non-scintillator portions are alternately arranged to provide a grating function to the scintillator panel, whereby the grating G2 and the scintillator portions (light-emitting portions) in the X-ray image detector are integrated. By doing this, as indicated in FIG. 2B, in an X-ray Talbot imaging apparatus using the scintillator panel according to the invention, the scintillator panel including the grating G2 can be disposed immediately near the sensor, as a result of which after formation of an interference pattern in the scintillator panel, most of the light reaches the sensor without scattering, so that a clear image is obtainable.

The scintillator panel according to the invention may have either a one-dimensional periodic structure or a two-dimensional periodic structure as long as the scintillator portions and the non-scintillator portions are alternately arranged.

Figure 3A:
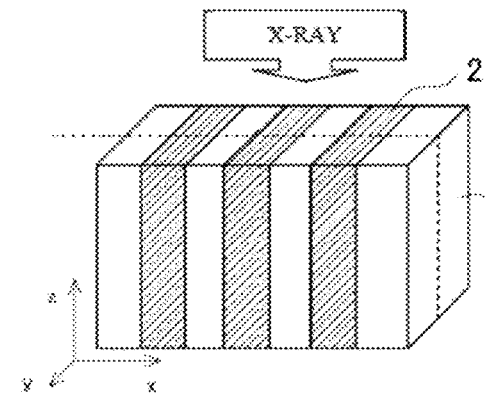
Figure 3B:
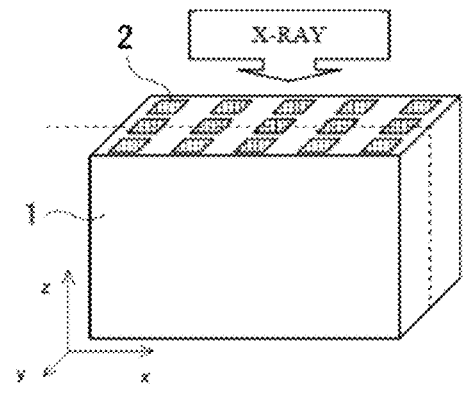

FIGS. 3A and 3B depict schematic diagrams depicting a scintillator panel having a one-dimensional periodic structure and a scintillator panel having a two-dimensional periodic structure.

The one-dimensional periodic structure is a structure in which when viewed from an X-ray irradiation direction (z-axis direction in FIG. 3A), linear scintillator portions 2 and linear non-scintillator portions 1 are alternately arranged, as indicated in FIG. 3A. The scintillator portions 2 and the non-scintillator portions 1 are preferably repeatedly arranged in a direction parallel to a y-z plane. The term "parallel" includes both "completely parallel" and "slightly inclined".

The two-dimensional periodic structure is a structure in which when viewed from an X-ray irradiation direction (z-axis direction in FIG. 3B), for example, a plurality of non-scintillator portions 1 are arranged in a transverse direction (x-axis direction) and a longitudinal direction (y-axis direction) and intersect with each other to partition the scintillator portions 2 into blocks, as indicated in FIG. 3B. The shape of the partitioned scintillator portions viewed from the X-ray irradiation direction is not particularly limited, and examples of the shape include a square, a rectangle, a parallelogram, and a trapezoid.

Figure 4:
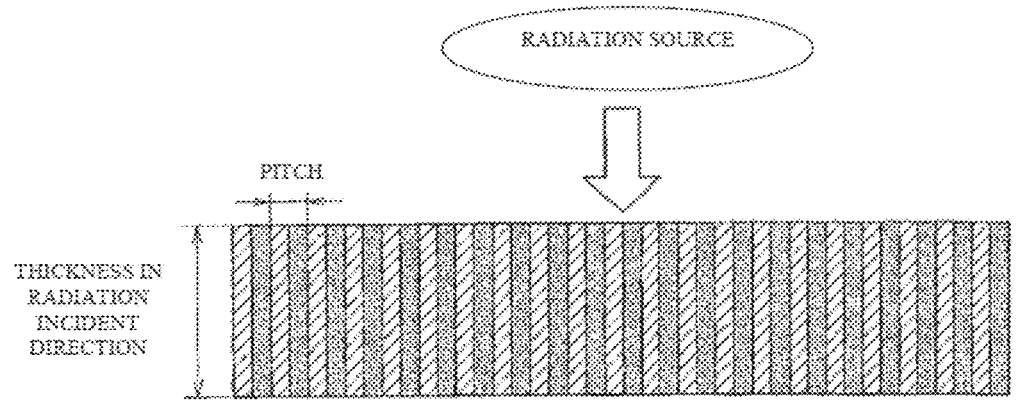
FIG. 4 is a schematic diagram depicting a pitch of a scintillator panel according to an embodiment of the invention and a thickness thereof in a radiation incident direction.
Figure 5A:
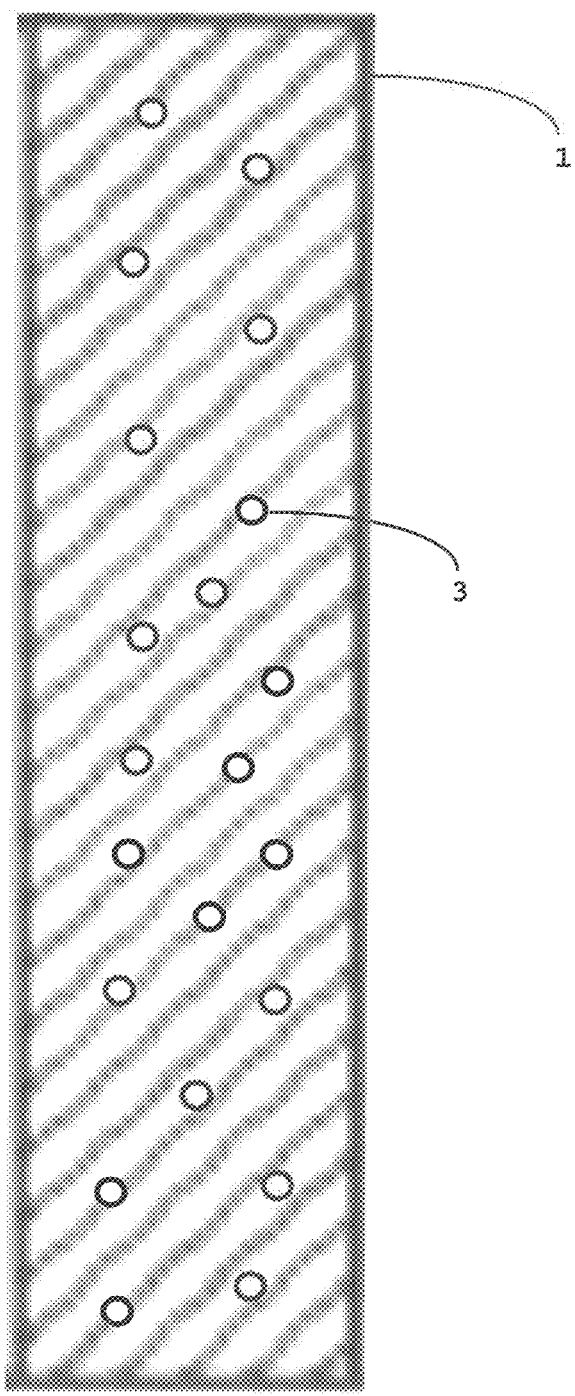
FIG. 5A illustrates an enlarged view of a scintillator portion according to an embodiment of the invention, in which gas 3 is uniformly included as a stress-relaxing portion in the scintillator portion 1.
Figure 5B:
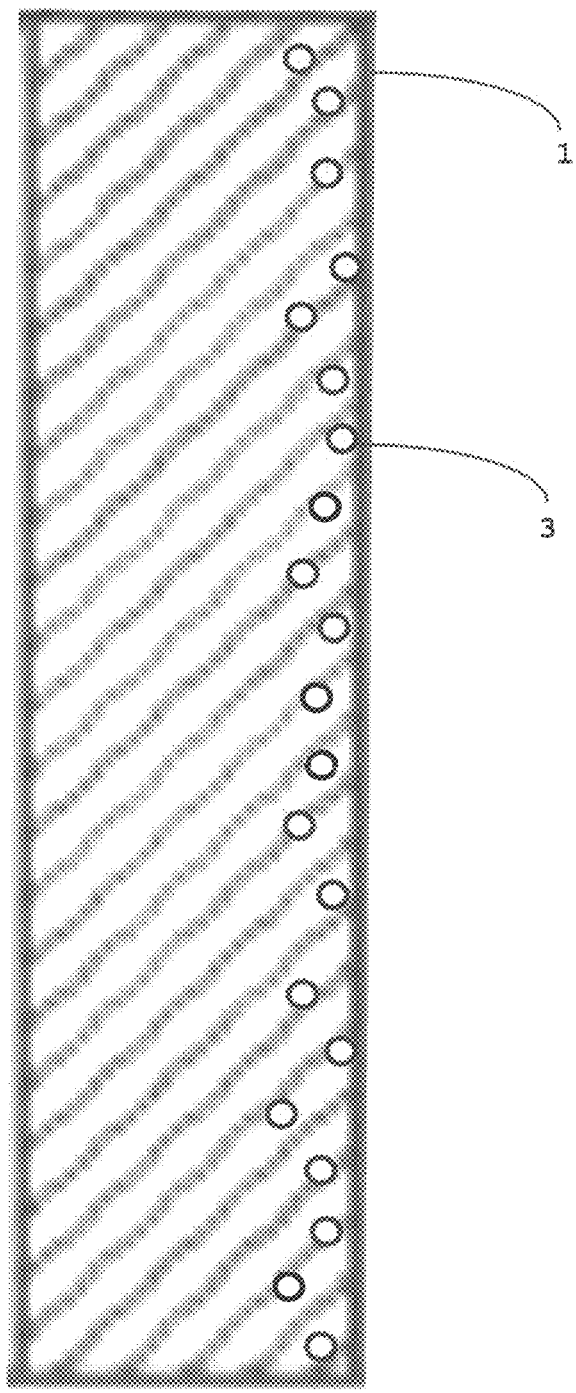
FIG. 5B illustrates an enlarged view of a scintillator portion according to an embodiment of the invention, in which gas 3 is included as a stress-relaxing portion on one side surface of the scintillator portion 1.
Figure 5C:
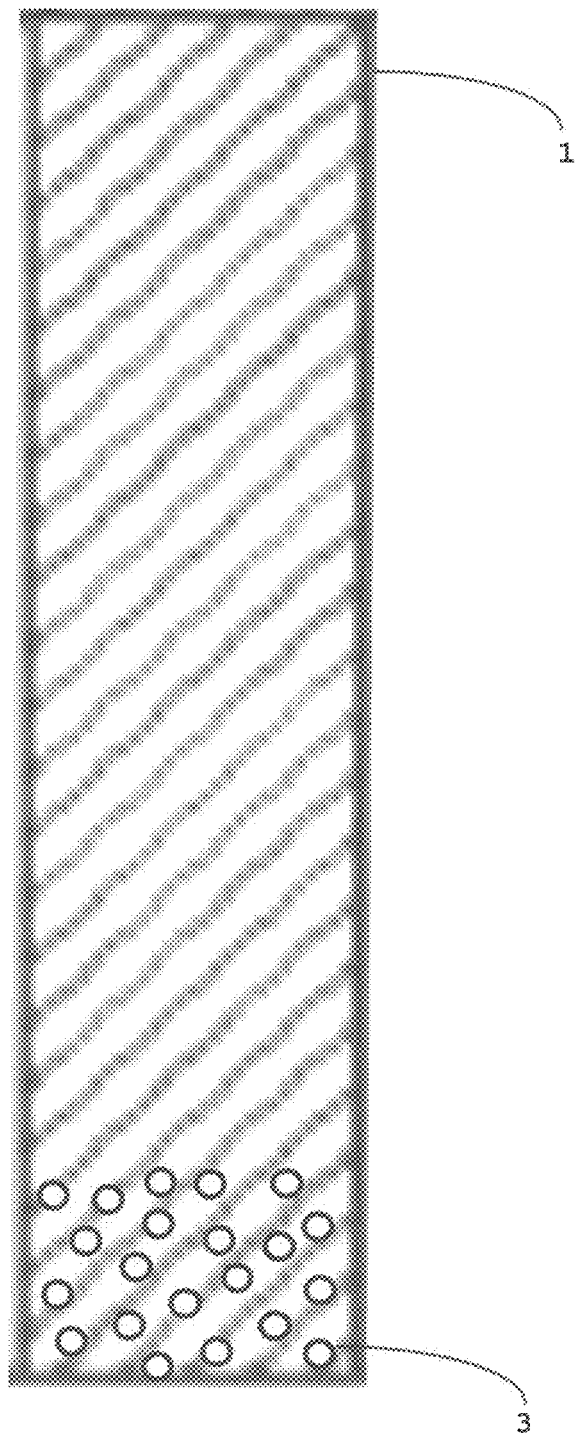
FIG. 5C illustrates an enlarged view of a scintillator portion according to an embodiment of the invention, in which gas 3 is included as a stress-relaxing portion on the bottom surface of the scintillator portion 1.

FIG. 4 depicts a total thickness of a pair of a scintillator portion and a non-scintillator portion (hereinafter also referred to as "pitch") and a thickness of the panel in a radiation incident direction. Additionally, the term "a pair" refers to an arbitrary pair of a scintillator portion and a non-scintillator portion that are adjacent to each other among the scintillator portions and the non-scintillator portions alternately arranged. In the scintillator panel illustrated in FIG. 4, there is depicted a cross-sectional view, for example, in a z-x direction cut along a dotted-line part of the scintillator panel having the one-dimensional periodic structure or the two-dimensional periodic structure illustrated in FIG. 3A or 3B.

A ratio of the pitch of the scintillator panel according to the invention and a thickness ratio of the pair of a scintillator portion and a non-scintillator portion (hereinafter also referred to as "duty ratio") are calculated from Talbot interference conditions, such as a tube voltage (energy) and a distance from a tube bulb. Typically, the pitch is from 0.5 to 50 μm, and the duty ratio (thickness of scintillator portions/thickness of non-scintillator portions) is from 30/70 to 70/30. The number of repetitions of the scintillator portions and the non-scintillator portions is preferably set to a value obtained by dividing an area necessary for a part to be imaged by the pitch. To obtain a diagnostic image having a sufficient area, the number of repetitions thereof is preferably from 1,000 to 500,000, with respect to 1 for a pair of a scintillator portion and a non-scintillator portion.

The thickness of the scintillator panel according to the invention in the radiation incident direction is preferably from 10 to 1,000 μm, and more preferably from 100 to 500 μm. When the thickness of the scintillator panel in the radiation incident direction is equal to or more than a lower limit value of the above range, the scintillator panel has sufficient light-emission intensity, improving image quality. Additionally, when the thickness thereof is equal to or less than an upper limit value of the above range, a distance taken for light emitted by the scintillator panel to reach the light-receiving sensor does not become too long, so that the light is not scattered and therefore sharpness reduction can be suppressed.

An aspect ratio between the thickness of the scintillator panel according to the invention in the radiation incident direction and the thickness of the non-scintillator portions is preferably from 10 to 300, more preferably from 28 to 300, and still more preferably from 50 to 200.

<Scintillator Portions>

The scintillator portions included in the scintillator panel according to the invention include a phosphor component and a stress-relaxing portion. The scintillator portions may include other components if needed.

<Phosphor Component>

As the phosphor component, a material capable of converting a radiation such as an X-ray to light having a different wavelength, such as visible light, can be used appropriately. Specific possible examples of the material include scintillators and phosphors described in a range of from pages 284 to 299 of "Phosphor Handbook (Japanese title: Keikotai Handobukku)" (edited by the Phosphor Research Society (Keikotai Dogakkai); published by Ohmsha (1987)) and materials described on the website homepage "Scintillation Properties (http://scintillator.lbl.gov/)" of the Lawrence Berkeley National Laboratory in the U.S. However, other materials not listed here can also be used as the phosphor component as long as the materials are capable of converting a radiation such as an X-ray to light having a different wavelength, such as visible light.

Specific examples of the composition of the phosphor component include compositions represented by basic composition formulae (I) to (VII) below.

Basic composition formula (I) below represents a composition of a metal halide phosphor.

$$M_I X \cdot a M_{II} X'_2 \cdot b M_{III} X''_3 : zA \qquad \text{Basic composition formula (I):}$$

In above basic composition formula (I), $M_I$ represents at least one selected from the group consisting of elements that can become monovalent cations, such as lithium (Li), sodium (Na), potassium (K), rubidium (Rb), cesium (Cs), thallium (Tl), and silver (Ag).

$M_{II}$ represents at least one selected from the group consisting of elements that can become divalent cations, such as beryllium (Be), magnesium (Mg), calcium (Ca), strontium (Sr), barium (Ba), nickel (Ni), copper (Cu), zinc (Zn), and cadmium (Cd).

$M_{III}$ represents at least one selected from the group consisting of scandium (Sc), yttrium (Y), aluminum (Al), gallium (Ga), indium (In), and elements belonging to lanthanoid.

X, X', and X" respectively represent a halogen element, and which halogen elements may be different or identical.

A represents at least one element selected from the group consisting of Y, Ce, Pr, Nd, Sm, Eu, Gd, Tb, Dy, Ho, Er, Tm, Yb, Lu, Na, Mg, Cu, Ag (silver), Tl, and Bi (bismuth).

a, b, and z each independently represent a numerical value in ranges of $0 \leq a \leq 0.5$, $0 \leq b \leq 0.5$, and $0 \leq z < 1.0$.

Basic composition formula (II) below represents a composition of a rare earth-activated metal fluoride halide phosphor.

$$M_{II} FX : zLn \qquad \text{Basic composition formula (II):}$$

In above basic composition formula (II), $M_{II}$, Ln and X represent at least one alkaline earth metal element, at least one element belonging to lanthanoid, and at least one halogen element, respectively. Additionally, z is in a range of $0 < z \leq 0.2$.

Basic composition formula (III) below represents a composition of a rare earth oxysulfide phosphor.

$$Ln_2 O_2 S : zA \qquad \text{Basic composition formula (III):}$$

In above basic composition formula (III), Ln represents at least one element belonging to lanthanoid, and A is the same as in above basic composition formula (I). In addition, z is in a range of $0 < z < 1$.

Particularly, gadolinium oxysulfide ($Gd_2O_2S$) using gadolinium (Gd) as Ln is preferable since it is known that, by using terbium (Tb), dysprosium (Dy), or the like as the element type of A, the compound exhibits high light-emitting characteristics in a wavelength range in which the light-receiving sensor receives light most easily.

Basic composition formula (IV) below represents a composition of a meal sulfide phosphor.

$$M_{II} S : zA \qquad \text{Basic composition formula (IV):}$$

In above basic composition formula (IV), $M_{II}$ represents an element that can become a divalent cation, in other words, at least one element selected from the group consisting of alkaline rare earth metals, Zn (zinc), Sr (strontium), Ga (gallium), and the like, and A is the same as in above basic composition formula (I). Additionally, z is in a range of $0 < z < 1$.

Basic composition formula (V) below represents a composition of a metal oxoacid-salt phosphor.

$$M_{IIa} (AG)_b : zA \qquad \text{Basic composition formula (V):}$$

In above basic composition formula (V), $M_{II}$ represents a metal element that can become a cation, (AG) represents at least one oxoacid group selected from the group consisting of phosphate, borate, silicate, sulfate, tungstate, and aluminate, and A is the same as in above basic composition formula (I).

Additionally, a and b represent all values that can be taken depending on valences of the metal and the oxoacid group. z is in a range of $0 < z < 1$.

Basic composition formula (VI) below represents a composition of a metal oxide phosphor.

$$M_a O_b : zA \qquad \text{Basic composition formula (VI):}$$

In above basic composition formula (VI), M represents at least one element selected from metal elements that can become cations, and A is the same as in above basic composition formula (I).

Additionally, a and b represent all values that can be taken depending on a valence of M. z is in a range of $0 < z < 1$.

Basic composition formula (VII) below represents a metal acid halide phosphor.

$$LnOX : zA \qquad \text{Basic composition formula (VII):}$$

In above basic composition formula (VII), Ln and X represent at least one element belonging to lanthanoid and at least one halogen element, respectively, and A is the same as in above basic composition formula (I). In addition, z is in a range of $0 < z < 1$.

Additionally, zA or zLn in above basic composition formulae (I) to (VII) represents an augmenting agent. The augmenting agent is preferably added as a halide of A or Ln.

A phosphor component content in 100% by volume of the scintillator portions is preferably from 50 to 98% by volume, more preferably from 65 to 98% by volume, and particularly preferably from 80 to 98% by volume. The phosphor component content can be measured, for example, by the following method.

First, the scintillator panel according to the invention is cut so that cross-sections of the scintillator portions can be seen. At this time, cutting is performed in such a manner as to expose a surface where alternate arrangement of the scintillator portions and the non-scintillator portions can be confirmed. Specifically, preferably, in the scintillator panel having the one-dimensional periodic structure, cutting is performed in such a manner as to expose a z-x plane in FIG. 3A, for example, a surface indicated by the dotted line, and in the scintillator panel having the two-dimensional periodic structure, cutting is performed in such a manner as to expose either the z-x plane or a y-z plane in FIG. 3B that is a surface where alternate arrangement of the non-scintillator portions and the scintillator portions can be confirmed, for example, a surface indicated by the dotted line.

Examples of methods for the cutting include a microtome and a cross section polisher (CP).

Then, the cross sections are observed by using a laser microscope or a scanning electron microscope (SEM). In the observation of the cross sections, usually, 20 or more blocks of scintillator portions are observed in a cross-sectional image. For each block, an area value of a phosphor portion is obtained by using image analysis software or the like, and from the area value, a phosphor component content in 100% by volume of the scintillator portions is calculated to calculate an average of phosphor portion contents in the 20 blocks of scintillator portions.

When the phosphor component content of the scintillator portions is in the above range, a sufficient stress-relaxing portion content can be secured while having sufficient luminance, which is thus preferable.

<Stress-Relaxing Portion>

The stress-relaxing portion is a portion that can relax stress generated in the scintillator panel. The scintillator panel according to the invention includes the stress-relaxing portion in the scintillator portions. Thus, for example, even when heat is generated during operation of the apparatus and thereby a thermal expansion difference occurs between the phosphor component and the partition walls, stress generated by the thermal expansion difference can be relaxed, so that local cracking, peeling of the phosphor component, or the like hardly occurs.

When a gas is present in the scintillator portions, the stress-relaxing portion refers to the gas, while when no gas is present in the scintillator portions, the stress-relaxing portion refers to resin. The expression "when a gas is present in the scintillator portions" refers to specifically when a gas content in 100% by volume of the scintillator portions is equal to or more than 1% by volume, and the expression "when no gas is present in the scintillator portions" refers to specifically when the gas content in 100% by volume of the scintillator portions is less than 1% by volume. The gas content can be measured, for example, in the same manner as the above phosphor component content.

The stress-relaxing portion is preferably a gas, from the viewpoint of enabling stress to be sufficiently relaxed.

The gas is not particularly limited as long as the gas remains gaseous at room temperature (20° C.). Examples of the gas include air, carbon dioxide gas, nitrogen gas, and inert gasses such as argon and helium gas.

The gases may be those generated by a foaming agent or those contained in hollow particles.

The gases may be used singly or two or more kinds thereof may be used.

The resin is not particularly limited as long as it is a resin, but the resin is preferably an adhesive resin that serves as a binder of the phosphor component. Additionally, the resin is preferably a material transparent to a wavelength of light emitted by the scintillator panel so as not to inhibit propagation of the light emitted by the scintillator panel.

Examples of the adhesive resin include natural polymer materials, such as proteins such as gelatin, polysaccharides such as dextran, and gum Arabic, and polymer materials, such as polyvinyl butyral, polyvinyl acetate, nitrocellulose, ethyl cellulose, copolymers of vinylidene chloride and vinyl chloride, poly(meth)acrylate, copolymers of vinyl chloride and vinyl acetate, polyurethane, cellulose acetate butyrate, polyvinyl alcohol, polyester, epoxy resins, polyolefin resins, and polyamide resins. In addition, these resins may be those crosslinked by a crosslinking agent such as epoxy or isocyanate.

The resins may be used singly or two or more kinds thereof may be used.

Additionally, the resins may be either thermoplastic resins or thermosetting resins.

A stress-relaxing portion content in 100% by volume of the scintillator portions is preferably from 2 to 50% by volume, more preferably from 2 to 35% by volume, and particularly preferably from 2 to 20% by volume. The stress-relaxing portion content in the scintillator portions can be measured, for example, by the same method as that for the phosphor component content described above. When the stress-relaxing portion content in the scintillator portions is in the above range, stress can be sufficiently relaxed even when generated in the scintillator panel.

The scintillator panel according to the invention includes the plurality of scintillator portions. The stress-relaxing portion contents of respective scintillator portions are preferably uniform between the plurality of scintillator portions so that luminance unevenness in an image is prevented. Specifically, a difference between the stress-relaxing portion contents of the respective scintillator portions is preferably within 8% by volume, more preferably within 5% by volume, and still more preferably within 3% by volume. The difference between the contents is obtained, for example, by calculating stress-relaxing portion contents of the 20 blocks of the scintillator portions by the same method as that for the above-described phosphor component content and calculating a difference between a maximum value and a minimum value among the stress-relaxing portion contents of the 20 blocks.

The scintillator panel according to the invention may include the stress-relaxing portion (1) on bottom surfaces of the scintillator portions, (2) on at least one of side surfaces of each scintillator portion, or (3) uniformly on an entirety of the each scintillator portion.

Herein, the bottom surface of each scintillator portion described above (1) refers to a surface where the scintillator portion contacts with a support when the scintillator panel includes the support. The side surface of the each scintillator portion described above (2) refers to at least one surface other than the bottom surface among the surfaces of the scintillator portion in contact with each non-scintillator portion.

In addition, a method for producing the scintillator panel in respective cases of the above (1) to (3) will be described later in the section of <<Method for Producing Scintillator Panel for X-ray Talbot Imaging Apparatus>>.

In the cases of (2) and (3) described above, when the scintillator portions are divided into three equal portions perpendicularly to the X-ray irradiation direction, a difference between respective stress-relaxing portion contents of the divided three scintillator portions is preferably equal to or less than 10% by volume, more preferably equal to or less than 8% by volume, and still more preferably equal to or less than 5% by volume. These can be measured by the same method as that for the phosphor component content described above.

<Other Component(s)>

The scintillator portions may include other component(s) if necessary.

Examples of the other component(s) include an additive(s) such as a dispersant, a thickener, a plasticizer, and/or a curing agent. Additionally, when the other component(s) is/are resin and so is the stress-relaxing portion, the resin(s) added as the other component(s) serve(s) also as the stress-relaxing portion.

Examples of the dispersant include phthalic acid, stearic acid, caproic acid, and lipophilic surfactants.

Examples of the thickener include polyethylene oxide, amides, and resin particles having a three-dimensional crosslinked structure. The dispersants and the thickeners can be used to improve dispersibility of the phosphor component.

Examples of the plasticizers include phosphate esters such as triphenyl phosphate, tricresyl phosphate, and diphenyl phosphate, phthalate esters such as diethyl phthalate and dimethoxy ethyl phthalate, glycolate esters such as ethyl phthalyl ethyl glycolate and butyl phthalyl butyl glycolate, and polyesters of polyethylene glycol and aliphatic dibasic acid, such as a polyester of triethylene glycol and adipic acid and a polyester of diethylene glycol and succinic acid.

Examples of the curing agent include those well known as curing agents for thermosetting resins, and can be used without particular limitations.

When using an adhesive resin, any of the plasticizers, the curing agents, and/or the like can be used to improve a coupling strength between the adhesive resin and the phosphor component in the scintillator panel.

<Non-Scintillator Portions>

The scintillator panel according to the invention includes the non-scintillator portions.

The non-scintillator portions preferably include, as a main component, at least one selected from glasses, ceramics, semiconductors, polymers, carbon fibers, glass fibers, metal foils, and bio-nanofibers. Here, the term "main component" refers to a component having a largest mass ratio among components included in the non-scintillator portions.

Examples of the glasses include quartz, borosilicate glass, and chemically reinforced glass.

Examples of the ceramics include sapphire, silicon nitride, and silicon carbide.

Examples of the semiconductors include silicon, germanium, gallium arsenide, gallium phosphide, and gallium nitride.

Examples of the polymers include polyesters such as polyethylene terephthalate (PET) and polyethylene naphthalate (PEN), aliphatic polyamides such as nylon, aromatic polyamides (aramids), polyolefins such as polyethylenes such as polyimide, polyamide-imide, and polyether imide and polypropylene, polycarbonate, triacetate, cellulose acetate, epoxy, bismaleimide, polylactic acid, sulfur-containing polymers such as polyphenylene sulfide and polyether sulfone, polyether ether ketone, fluororesin, acrylic resin, and polyurethane.

As for the carbon fibers and the glass fibers, particularly preferred are fiber-reinforced resin sheets including these fibers.

Examples of the metal foils include aluminum, iron, and copper.

Examples of the bio-nanofibers include bio-nanofibers including chitosan, cellulose, and/or the like.

These may be used singly or two or more kinds thereof may be used.

When arranging the scintillator portions and the non-scintillator portions in the one-dimensional periodic structure, the non-scintillator portions are preferably made of polymer, and particularly preferably made of polyester such as PET, from the viewpoint of handling in production.

When arranging the scintillator portions and the non-scintillator portions in the two-dimensional periodic structure, the non-scintillator portions are preferably made of semiconductor, and particularly preferably made of silicon, from the viewpoint of processability.

Additionally, the non-scintillator portions are preferably transparent to the wavelength of light emitted from the phosphor component. By using transparent non-scintillator portions, light emitted from the phosphor component is propagated not only to the scintillator portions but to the non-scintillator portions, whereby the amount of light reaching the sensor is increased, thus improving luminance. In the arrangement of the scintillator portions and the non-scintillator portions in the one-dimensional periodic structure, a transmittance of light emitted from the phosphor component in the non-scintillator portions is preferably equal to or more than 80%.

<Support>

The scintillator panel according to the invention preferably includes a support.

The support may be made of a component identical to or different from that of the non-scintillator portions. Additionally, the non-scintillator portions and the support may be integrated.

Preferably, the support enables radiation such as X-rays to be transmitted therethrough.

Examples of the support that can be used include a plate glass made of quartz, borosilicate glass, chemically reinforced glass, or the like, a ceramic substrate made of sapphire, silicon nitride, silicon carbide, or the like, a semiconductor substrate (a photoelectric converter panel) made of silicon, germanium, gallium arsenic, gallium phosphide, gallium nitride, or the like, a polymer film (a plastic film) such as a cellulose acetate film, a polyester film, a polyethylene terephthalate film, a polyamide film, a polyimide film, a triacetate film, a polycarbonate film, or the like, a metal sheet such as an aluminium sheet, an iron sheet, a copper sheet, or the like or a metal sheet having a coat layer made of an oxide of any of the metals, a carbon fiber-reinforced resin (CFRP) sheet, and an amorphous carbon sheet.

A thickness of the support is preferably from 50 to 2,000 μm, and more preferably from 50 to 1,000 μm.

When integrating the non-scintillator portions with the support, for example, patterning of concave portions is performed on a member made of any of the above components, thereby enabling production of a member in which the non-scintillator portions and the support are integrated.

When the non-scintillator portions and the support are not integrated, for example, an adhesive can be used for adhesion.

Between the non-scintillator portions and the scintillator portions and the support may be provided a layer that reflects or absorbs light emitted by the scintillator panel, if necessary. Providing the layer that reflects light emitted by the scintillator panel improves luminance, and providing the layer that absorbs the light emitted thereby improves sharpness. The support itself may be provided with a function of reflecting or absorbing light emitted by the scintillator panel.

<<Method for Producing Scintillator Panel for X-Ray Talbot Imaging Apparatus>>

A method for producing the scintillator panel according to the invention is classified into three cases depending on a location of the stress-relaxing portion included in the scintillator portions: (1) a case in which the stress-relaxing portion is present on the bottom surfaces of the scintillator portions; (2) a case in which the stress-relaxing portion is present on at least one of side surfaces of each scintillator portion; and (3) a case in which the stress-relaxing portion is uniformly present on an entirety of the scintillator portions.

(1) The Case in which the Stress-Relaxing Portion is Present on the Bottom Surfaces of the Scintillator Portions When producing the scintillator panel (1) including the stress-relaxing portion present on the bottom surfaces of the scintillator portions, it is preferable to use a member in which the support and the non-scintillator portions are integrated. Additionally, the stress-relaxing portion included in the scintillator panel (1) is preferably a gas.

The member in which the support and the non-scintillator portions are integrated (for example, a silicon wafer or the like) can be produced, for example, by performing patterning on a member surface by photolithography and immersing the member in a process liquid containing potassium hydroxide, hydrogen fluoride, or the like to perform etching (wet-etching process). Additionally, the member in which the support and the non-scintillator portions are integrated can also be produced, for example, by performing patterning on the member surface by photolithography and then performing a reactive ion-etching using a gas of sulfur hexafluoride ($SF_6$) or the like (dry-etching process). Depending on the shape of patterning of the concave portions, the scintillator portions and the non-scintillator portions can be arranged either in a one-dimensional periodic structure or a two-dimensional periodic structure.

As the method for producing the scintillator panel in the above (1), for example, the phosphor component is poured into the concave portions of the member in which the support and the non-scintillator portions are integrated produced by the above method, under an atmospheric pressure of preferably from 0.12 to 1 and more preferably from 0.15 to 0.6. To adjust to the above atmospheric pressure, a vacuum chamber at reduced pressure is preferably used to place the panel in the vacuum chamber at reduced pressure and pour the phosphor component.

The phosphor component is not particularly limited, but is preferably a phosphor component including cesium iodide, from the viewpoint of operability, luminance, and the like. In addition, from the viewpoint of pouring, the phosphor component is desirably heated to a temperature at which the phosphor component is dissolved.

The phosphor component may be poured by mixing with a foaming agent, hollow particles, resin, and/or the like, if necessary.

When pouring the phosphor component in the concave portions of the member in which the support and the non-scintillator portions are integrated under the above atmospheric pressure, a gas such as air remains in the concave portions of the member and the phosphor component is poured on an upper part of the gas. In this state, cooling or the like is performed to fix the phosphor component, thereby enabling production of the scintillator panel (1) including the gas as the stress-relaxing portion on the bottom surfaces of the scintillator portions.

In the scintillator panel (1) produced above, a bonding end surface thereof is preferably flattened after production. Particularly, by flattening a surface of the panel on a side facing the light-receiving sensor (a surface thereof on a side where the support is not provided), scattering of light on the bonding end surface can be suppressed, thus improving sharpness. The method for flattening is not particularly limited, and, other than mechanical machining, such as cutting, grinding, and polishing, radiation of energy such as ion, plasma, or electron beams may be performed.

(2) The Case in which the Stress-Relaxing Portion is Present on at Least One of Side Surfaces of Each Scintillator Portion When Producing a Scintillator Panel (2) Including the Stress-Relaxing Portion on at Least One of the Side surfaces of each scintillator portion, it is preferably a scintillator panel in which the scintillator portions and the non-scintillator portions are one-dimensionally laminated. Additionally, the stress-relaxing portion included in the scintillator panel (2) is preferably a gas.

In addition, when producing the scintillator panel (2), the non-scintillator portions are preferably made of a film of polymer and/or the like.

In the scintillator panel (2), for example, a composition including a phosphor component and preferably an adhesive resin is coated on a non-scintillator portion made of a film or the like, whereby a scintillator portion can be produced on the non-scintillator portion. The composition may be coated on both surfaces of the non-scintillator portion.

When the composition is coated on the non-scintillator portion, particles of the phosphor component are exposed on a surface of a layer formed of the composition, and due to that and other factors, concave-convex portions are formed on the surface of the layer. The non-scintillator portion or the non-scintillator portion coated on the surface thereof are repeatedly laminated on an upper part of the layer until a desired thickness is obtained, and for example, heating, pressurization, and/or the like are/is performed to enable a scintillator panel to be produced. In this case, since the concave-convex portions are formed on the surface of the layer, spaces are provided between the layer and each of the non-scintillator portions, so that scintillator portions including the spaces (the stress-relaxing portion) can be produced.

In addition, for example, a roughening treatment such as blasting or embossing may be performed on the surfaces of the scintillator portions or the non-scintillator portions to provide spaces.

The composition includes a phosphor component, and preferably, additionally includes an adhesive resin. An amount of the resin contained in a solid content in the composition is preferably from 4.5 to 20% by mass, and more preferably from 7.5 to 20% by mass. Additionally, the solid content refers to a component obtained by removing a solvent from the composition.

In coating the composition on the non-scintillator portions, there may be mentioned a case of coating of a composition prepared by dissolving or dispersing the phosphor component and the like in a solvent added into the above composition and a case of coating of the above composition heated and melted. Preferred is coating of the composition containing the phosphor component and the like dissolved or dispersed in the solvent added into the above composition.

Examples of the solvent include lower alcohols such as methanol, ethanol, isopropanol, and n-butanol; ketones such as acetone, methyl ethyl ketone, methyl isobutyl ketone, and cyclohexanone; esters of lower fatty acids and lower alcohols, such as methyl acetate, ethyl acetate, and n-butyl acetate; aromatic compounds, such as ethers such as dioxane, ethylene glycol monoethyl ether, and ethylene glycol monomethyl ether, triol, and xylol; and halogenated hydrocarbons such as methylene chloride and ethylene chloride. The solvents may be used singly or two or more kinds thereof may be used.

In coating the above composition after heating and melting, a hot melt resin is preferably added, as an adhesive resin, into the composition. Examples of the hot melt resin include resins whose main component is a resin such as polyolefin, polyamine, polyester, polyurethane, or acryl. Additionally, the term "main component" refers to a component having a largest mass ratio among components included in a resin. Among them, preferred are resins including a polyolefin resin as the main component, from the viewpoint of light transmittance, moisture-proofness, and adhesiveness. Examples of the polyolefin resin that can be used include ethylene-vinyl acetate copolymers (EVA), ethylene-acrylic acid copolymers (EAA), ethylene-acrylate copolymers (EEA), ethylene-methacrylic acid copolymers (EMAA), ethylene-methacrylate copolymers (EMMA), and ionomer resins. In addition, these resins may be used as a so-called polymer blend that stands for a combination of two or more kinds thereof.

The method for coating the composition is not particularly limited, and a usual coating method, for example, such as a doctor blade, a roll coater, a knife coater, an extrusion coater, a die coater, a gravure coater, a lip coater, a capillary coater, or a bar coater, can be used.

In addition, after repeatedly laminating the scintillator portions and the non-scintillator portions (hereinafter also referred to as "laminate"), a step of bonding both portions is preferably included.

As the bonding method, for example, both portions can be closely contacted by pressurization. Additionally, by heating in the pressurized state, an adhesive material is melted or cured to strengthen adhesion, which is more preferable.

The method for pressurizing is not particularly limited. However, pressurization is preferably performed in a state where a spacer made of metal or the like is provided in advance so that the laminate is not compressed to a size smaller than a desired size. In this case, by providing the spacer so as to have a thickness of preferably from 100 to 120%, and more preferably from 102 to 108% with respect to a theoretical film thickness of the scintillator panel calculated by "a film thickness of a pair of a scintillator portion and a non-scintillator portion"×"the number of laminated layers", lamination can be made without crushing and eliminating the spaces formed between the phosphor component-containing layer and the non-scintillator portions, which is thus preferable. In addition, when the composition includes a solvent, the film thickness of the scintillator portion that is used to calculate the theoretical film thickness of the scintillator panel refers to a film thickness of a layer that is obtained from the composition which has been coated on the non-scintillator portion, and from which preferably the solvent has been removed but which has not been heated yet.

The method for heating the laminate while pressurizing is not particularly limited. A press machine equipped with a heating element may be used, or the laminate may be enclosed in a box-shaped jig and heated in an oven in the enclosed state so as to have a predetermined size. The box-shaped jig may be equipped with a heating element.

Then, the laminate is preferably heated. The method for heating depends on the kind of the resin included in the composition. Heating is performed at a temperature of equal to or more than a glass transition point in the case of a thermoplastic resin, and at a temperature of equal to or more than a curing temperature in the case of a thermosetting resin, both preferably for approximately from 0.5 to 24 hours. The heating temperature is typically preferably from 40 to 250° C. When the temperature is equal to or more than a lower limit value of the range, fusion or curing reaction of the resin sufficiently proceeds, and bonding failure or the like hardly occurs. When the temperature is equal to or less than an upper limit value of the range, there hardly occurs a situation where the resin degenerates and optical characteristics are deteriorated.

Then, the bonding end surface of the laminate is preferably flattened. Particularly, by flattening a surface thereof positioned on a radiation incident side, a surface opposite to the surface, or both of the surfaces, scattering of light from the phosphor component on the bonding end surface can be suppressed, thereby improving sharpness. Examples of flattening methods that can be employed include the methods described in the section of the scintillator panel (1). In addition, in the case of mechanical machining, machining is preferably performed in a direction parallel to a lamination structure so that the lamination structure of the scintillator portions and the non-scintillator portions is not damaged.

The scintillator panel (2) preferably includes a support. Thus, for example, the laminate produced by the above method is preferably attached to the support.

The method for attaching the laminate to the support is not particularly designated. For example, an adhesive agent, a double-sided tape, a hot melt sheet, or the like can be used. After the attachment, flattening processing may be performed on a surface opposite to the bonding surface.

(3) The Case in which the Stress-Relaxing Portion is Uniformly Present on the Entirety of the Scintillator Portions A scintillator panel (3) in which the stress-relaxing portion is uniformly present on the entirety of the scintillator portions can be basically produced in the same manner as in the scintillator panel (2) including the stress-relaxing portion on at least one of the side surfaces of each scintillator portion.

However, a method for producing the scintillator panel (3) particularly preferably includes a step of pressurizing while heating in order to bond both the scintillator portions and the non-scintillator portions after repeatedly laminating in the method for producing the scintillator panel (2). The pressure at this time is preferably more intensified than in the method for producing the scintillator panel (2). In this case, by providing a spacer so as to have a thickness of preferably 99% or less, and more preferably from 80 to 98% with respect to the theoretical film thickness of the scintillator panel, the spaces formed between the phosphor component-containing layer and the non-scintillator portions are crushed and most of the spaces are eliminated. Accordingly, unlike the scintillator panel (2), the scintillator panel (3) does not include the stress-relaxing portion locally on at least one of the side surfaces of each scintillator portion, and for example, spaces between the particles of the phosphor component provided by a method described later serve as the stress-relaxing portion, so that the stress-relaxing portion can be uniformly provided on the entirety of the scintillator portions.

In the scintillator panel (3), in addition to the phosphor component, an adhesive resin is preferably added into a composition used to form the scintillator portions by coating on the non-scintillator portions. Additionally, the composition may include a foaming agent and/or hollow particles, if necessary.

In this case, by adding a large amount of an adhesive resin into the composition so that no air is present in the scintillator portions, the scintillator panel may include the resin as the stress-relaxing portion.

However, preferably, a small amount of an adhesive resin is added into the composition. Specifically, an adhesive resin content included in a solid content in the composition is preferably from 3.0 to 7.5% by mass, more preferably from 3.0 to 6.8% by mass, and still more preferably from 3.5 to 4.5% by mass. In this manner, when the composition including a small amount of an adhesive resin content is coated on the non-scintillator portions, spaces are created between the particles of the phosphor component, as a result of which the spaces can serve as the stress-relaxing portion.

[Image Detecting Panel for X-Ray Talbot Imaging Apparatus]

The image detecting panel for an X-ray Talbot imaging apparatus according to the present invention includes a light-receiving sensor and the above-described scintillator panel. Typically, the image detecting panel additionally includes an electric circuit, a battery, and the like.

The light-receiving sensor plays a role of capturing an image of light emitted from the scintillator panel. Examples of the light-receiving sensor include visible light CCD (charge coupled device) image sensors and CMOS (complementary metal oxide semiconductor) image sensors.

In the image detecting panel, preferably, the light-receiving sensor and the scintillator panel are optically coupled. The phrase "optically coupled" refers to being coupled so that loss of the amount of light due to scattering, reflection, and/or absorption is further reduced between the scintillator panel and the light-receiving sensor than when simply allowing the scintillator panel to be contacted with the light-receiving sensor. One specific example of the optical coupling is bonding between the scintillator panel and the light-receiving sensor with a transparent material having a larger refractive index than 1 (air).

In the image detecting panel, when the scintillator panel includes a support, the light-receiving sensor is preferably coupled to a side of the scintillator panel not including the support.

[X-Ray Talbot Imaging Apparatus]

An X-ray Talbot imaging apparatus according to the present invention includes the above-described scintillator panel. The X-ray Talbot imaging apparatus preferably includes a light-receiving sensor, in addition to the scintillator panel. In other words, the X-ray Talbot imaging apparatus preferably includes the above-described image detecting panel for an X-ray Talbot imaging apparatus.

Preferably, the X-ray Talbot imaging apparatus has a structure in which an X-ray source, diffraction gratings for Talbot (grating G0, grating G1, etc.), the scintillator panel, and the light-receiving sensor are arranged in this order. More preferably, the X-ray Talbot imaging apparatus is structured by additionally including an X-ray power supply unit that supplies power to the X-ray source, a camera control unit that controls image capturing operation of the light-receiving sensor, a processing unit that controls an entire operation of the X-ray Talbot imaging apparatus, and an X-ray control unit that controls X-ray irradiating operation in the X-ray source by controlling operation of the X-ray power supply unit.

The X-ray source is a device that emits X-rays to irradiate the Talbot diffraction gratings with the X-rays. The X-ray source is a device that emits X-rays, for example, by allowing a high voltage supplied from the X-ray power supply unit to be applied between a cathode and an anode so that electrons discharged from cathode filaments collide with the anode.

The diffraction gratings for Talbot are transmitting diffraction gratings that generate a Talbot effect by X-rays emitted from the X-ray source. The diffraction gratings for Talbot are preferably structured by including a tabular substrate made of an X-ray transmitting material and a plurality of diffraction members formed on a surface of one side of the substrate. The substrate of the diffraction gratings for Talbot is made of, for example, glass, and the diffraction members are made of, for example, gold (Au). The diffraction gratings for Talbot are formed so as to satisfy conditions that generate the Talbot effect, and are far more coarse gratings than a wavelength of X-rays emitted from the X-ray source, for example, phase diffraction gratings whose grating constants (periods of the diffraction gratings) "d" are approximately 20 times or more than the wavelength of the X-rays. In addition, the diffraction gratings for Talbot may be amplitude (absorption) diffraction gratings that are similar in function.

The scintillator panel has a role of the integrated grating G2 and scintillator in the conventional Talbot system. In addition, when capturing an image of an object, the object is usually arranged between the grating G0 and the grating G1, and X-ray diffraction by the object can be visualized as moiré fringes by using the scintillator panel and the light-receiving sensor.

In the X-ray Talbot imaging apparatus using the scintillator panel according to the invention, even when heat is generated from the light-receiving sensor or the like during operation of the apparatus, the stress-relaxing portion in the scintillator portions can relax stress generated due to a thermal expansion difference between the phosphor component and the partition walls. Thus, local cracking or peeling of the phosphor component hardly occurs.

EXAMPLES

Hereinafter, the present invention will be described by Examples. However, the invention is not limited thereto.

[Stress-Relaxing Portion Content, Phosphor Component Content, and Difference Between Stress-Relaxing Portion Contents]

Each of scintillator panels produced in Examples and a Comparative Example below was cut by using a cross section polisher (CP) so as to expose a surface that allowed for confirmation of an alternate arrangement of non-scintillator portions and scintillator portions.

Then, the cross section was observed by using a scanning electron microscope (SEM). In the obtained cross-sectional image, area values of a stress-relaxing portion and a phosphor component were obtained by using image analysis software to calculate a stress-relaxing portion content and a phosphor component content in 100% by volume of the scintillator portions. Here, the calculated contents were average values in 20 blocks of the scintillator portions.

A difference between stress-relaxing portion contents was obtained by calculating a difference between a maximum value and a minimum value of the stress-relaxing portion contents of the 20 blocks obtained by the above method.

When each scintillator panel was divided into three equal portions perpendicularly with respect to the X-ray irradiation direction, a difference between respective stress-relaxing portion contents of the divided three scintillator portions was obtained by the following method.

After cutting the each scintillator panel by using a CP as above, the cross section was observed by using a scanning electron microscope (SEM). The scintillator portions in the cross-sectional image were divided into three equal portions (upper, middle, and lower portions) perpendicularly with respect to the X-ray irradiation direction. Area values of the stress-relaxing portions included in each portion were obtained by using image analysis software, and stress-relaxing portion contents in each portion were calculated from the area values. Here, the contents were calculated for 20 blocks of the scintillator portions, and an average value was calculated for the respective upper, middle, and lower portions of the scintillator portions. Among the stress-relaxing portion contents of the upper, middle, and lower portions in the scintillator portions calculated in this manner, a difference between a maximum value and a minimum value was defined as the difference between the contents.

[Temperature Change Test]

Each of the scintillator panels produced in the Examples and the Comparative Example below was placed in a constant temperature and humidity chamber (PR-3K, manufactured by ESPEC Corp.), subjected to temperature change from 5 to 50° C. in 10 minutes, and a presence or absence of cracking and/or peeling in the scintillator portions was confirmed visually and by a laser microscope (OLS4100, manufactured by Olympus Corp).

Example 1

A silicon wafer, 8 cm in diameter×8 cm×0.3 mm in thickness, was subjected to lattice patterning so that etched parts 3×3 μm☐(square) were formed at intervals of 3.5 μm on a surface of the wafer, and a concave-convex structure having a depth of 100 μm was produced by reactive ion etching (RIE) using $SF_6$ gas.

The silicon wafer having the patterned concave portions was placed in a vacuum chamber at reduced pressure, and a pressure inside the chamber was reduced to an atmospheric pressure of 0.5. After that, thallium-doped cesium iodide: CsI(Tl) dissolved by heating to 630° C. in a crucible in the chamber was poured into the concave portions of the silicon wafer. Here, the CsI(Tl) used was a commercially available product produced by adding 0.3% by mole of thallium iodide (TlI) to 100% by mole of cesium iodide (CsI). Then, the silicon wafer was gradually cooled to room temperature and taken out from the chamber. The surface of the silicon wafer was flattened by cutting by lathe machining to produce a scintillator panel.

The produced scintillator panel had air as a stress-relaxing portion on bottom surfaces of the scintillator portions. A stress-relaxing portion (air) content and a phosphor component content in 100% by volume of the scintillator portions in the produced scintillator panel were 20% by volume and 80% by volume, respectively, and a difference between the respective stress-relaxing portion contents was 5% by volume.

Additionally, as a result of the temperature change test, no cracking or peeling occurred in the scintillator portions.

Example 2

Particles of $Gd_2O_2S$:Tb having an average particle size of 2 μm and a polyester resin (VYLON 200 manufactured by Toyobo Co., Ltd., Tg=67° C.) were mixed in a methyl ethyl ketone solvent to give a solid content ratio (a $Gd_2O_2S$:Tb/polyester resin mass content ratio) of 95/5, whereby a composition was obtained. The composition was coated on a PET film (a non-scintillator portion) having a thickness of 3 μm by using a die coater to give a film thickness of 3 μm, whereby a partial laminate composed of the scintillator portion and the non-scintillator portion was produced. Then, the partial laminate was cut into pieces having a size of 120 mm×3 mm, 20,000 pieces of which were laminated.

Next, the laminate was pressurized in parallel to a laminate surface under a pressure condition of 0.2 GPa by using a metal jig so that the laminate had a film thickness of 125 mm corresponding to 105% with respect to a theoretical film thickness ((3 μm+3 μm)×20,000 layers=120 mm). Furthermore, in this state, the laminate was heated at 100° C. for 1 hour to produce a laminate block (120 mm×125 mm×3 mm) of 20,000 layers.

One side (a 120 mm×125 mm surface) of the laminate block was flattened by lathe machining, then coated with an epoxy adhesive, and attached to a CFRP plate having a thickness of 0.3 mm. After that, the laminate block was cut by lathe machining until the thickness of the block became 0.3 mm to obtain a laminated scintillator panel (120 mm×125 mm×0.3 mm).

The produced scintillator panel had air as a stress-relaxing portion on the one side surface of the scintillator portions in contact with the non-scintillator portions. A stress-relaxing portion (air) content and a phosphor component content in 100% by volume of the scintillator portions in the produced scintillator panel were 10% by volume and 90% by volume, respectively, and a difference between the respective stress-relaxing portion (air) contents was 2% by volume. When the scintillator portions were divided into three equal portions perpendicularly with respect to the X-ray irradiation direction, a difference between the respective stress-relaxing portion (air) contents of the divided three scintillator portions was 3% by volume.

Additionally, as a result of the temperature change test, no cracking or peeling occurred in the scintillator portions.

Example 3

A scintillator panel was produced in the same manner as Example 2 except that the particles of terbium-doped gadolinium oxysulphide ($Gd_2O_2S$:Tb) having the average particle size of 2 μm and the polyester resin (VYLON 200 manufactured by Toyobo Co., Ltd., Tg=67° C.) were mixed in a methyl ethyl ketone solvent to give a solid content ratio (a $Gd_2O_2S$:Tb/polyester resin mass content ratio) of 96/4, whereby a composition was obtained, and that a laminate composed of scintillator portions and non-scintillator portions was pressurized in parallel to a laminate surface under the pressure condition of 0.2 GPa by using a metal jig so that the laminate had a film thickness of 117 mm corresponding to 98% with respect to the theoretical film thickness 120 mm, and furthermore, in this state, the laminate was heated at 100° C. for 1 hour.

The scintillator panel produced above had spaces (air) between the particles of the phosphor component in the scintillator portions.

The scintillator panel had a stress-relaxing portion (air) content of 15% by volume and a phosphor component content of 85% by volume in 100% by volume of the scintillator portions, and a difference between the respective stress-relaxing portion (air) contents was 3% by volume. When the scintillator portions were divided into three equal portions perpendicularly with respect to the X-ray irradiation direction, a difference between the respective stress-relaxing portion (air) contents of the divided three scintillator portions was 4% by volume.

Additionally, as a result of the temperature change test, no cracking or peeling occurred in the scintillator portions.

Comparative Example 1

A scintillator panel was produced in the same manner as Example 1 except that the pressure inside the chamber was reduced to an atmospheric pressure of 0.1 as a monitor value, CsI(Tl) was poured into the concave portions of a silicon wafer, and nitrogen was introduced into the chamber to give atmospheric pressure, followed by gradual cooling to room temperature.

The produced scintillator panel had a gas content of 0.7% by volume and a phosphor component content of 99.3% by volume in 100% by volume of the scintillator portions.

Additionally, as a result of the temperature change test, cracking and/or peeling occurred in the scintillator portions.

Although embodiments of the present invention have been described and illustrated in detail, it is clearly understood that the same is by way of illustration and example only and not limitation, the scope of the present invention should be interpreted by terms of the appended claims.

What is claimed is:

1. A scintillator panel for an X-ray Talbot imaging apparatus, comprising alternately arranged scintillator portions and non-scintillator portions, the scintillator portions including a stress-relaxing portion, wherein the stress-relaxing portion is composed of a gas.

2. The scintillator panel for an X-ray Talbot imaging apparatus according to claim 1, wherein a stress-relaxing portion content in 100% by volume of the scintillator portions is from 2 to 50% by volume.

3. The scintillator panel for an X-ray Talbot imaging apparatus according to claim 1, wherein, in the scintillator portions arranged in plurality, a difference between stress-relaxing portion contents of respective scintillator portions is within 8% by volume.

4. The scintillator panel for an X-ray Talbot imaging apparatus according to claim 1, wherein the stress-relaxing portion is provided on at least one of a bottom surface and side surfaces of each scintillator portion.

5. The scintillator panel for an X-ray Talbot imaging apparatus according to claim 1, wherein when the scintillator portions are divided into three equal portions perpendicularly with respect to an X-ray irradiation direction, a difference between respective stress-relaxing portion contents of the divided three scintillator portions is within 8% by volume.

6. An image detecting panel for an X-ray Talbot imaging apparatus, comprising a light-receiving sensor and the scintillator panel for an X-ray Talbot imaging apparatus according to claim 1, the light-receiving sensor and the scintillator panel for an X-ray Talbot imaging apparatus being optically coupled.

7. An X-ray Talbot imaging apparatus comprising the scintillator panel for an X-ray Talbot imaging apparatus according to claim 1.

* * * * *